(12) United States Patent
Kosai et al.

(10) Patent No.: US 8,709,812 B2
(45) Date of Patent: Apr. 29, 2014

(54) DRUG COMPRISING AS THE ACTIVE INGREDIENT PROLIFERATIVE VECTOR CONTAINING SURVIVIN PROMOTER

(75) Inventors: Kenichiro Kosai, Kagoshima (JP);
Jyunichi Kamizono, Kagoshima (JP);
Satoshi Nagano, Kagoshima (JP)

(73) Assignee: Kenichiro Kosai, Kagoshima (JP)

( * ) Notice: Subject to any disclaimer, the term of this patent is extended or adjusted under 35 U.S.C. 154(b) by 0 days.

(21) Appl. No.: 13/426,048

(22) Filed: Mar. 21, 2012

(65) Prior Publication Data
US 2012/0230954 A1    Sep. 13, 2012

Related U.S. Application Data

(63) Continuation of application No. 11/569,625, filed as application No. PCT/JP2005/009818 on May 23, 2005, now Pat. No. 8,142,770.

(30) Foreign Application Priority Data

May 25, 2004   (JP) ................. 2004-154431

(51) Int. Cl.
*A61K 48/00*  (2006.01)
*C12N 5/00*  (2006.01)
*C12N 15/00*  (2006.01)
*C12N 15/09*  (2006.01)
*C12N 15/33*  (2006.01)

(52) U.S. Cl.
USPC ......... 435/455; 424/93.2; 424/93.21; 514/44; 435/325

(58) Field of Classification Search
None
See application file for complete search history.

(56) References Cited

U.S. PATENT DOCUMENTS

2003/0099616 A1 *  5/2003  Irving et al. ............... 424/93.2

OTHER PUBLICATIONS

Evans et al, Gene therapy of the rheumatic diseases: 1998 to 2008, online at http://arthritis-research.com/content/11/1/209.*
Thomas et al, Progress and Problems With the Use of Viral Vectors for Gene Therapy, Nature, 346 I May 2003, vol. 4, pp. 346-358.*
Verma and Somia, Gene Therapy—promises, problems and prospects, Nature, 1997, vol. 389, pp. 239-242.*
Russell, S. J., Replicating Vectors for Gene Therapy of Cancer: Risks, Limitations and Prospects, European J Cancer, 1994, vol. 30A (8), pp. 1165-1171.*
Kami et al. "Development of the treatment for pancreatic cancer using surviving promoter-based conditionally replicative HSV-1 vector" *Journal of Japanese Society of Gastroenterology* 101: p. A179, No. 096, Mar. 20, 2004.

* cited by examiner

*Primary Examiner* — Maria Marvich
(74) *Attorney, Agent, or Firm* — Cesari and McKenna, LLP

(57) ABSTRACT

It is intended to provide a drug to be used in gene therapy which specifically targets abnormal cells such as tumor cells and destroys the same for healing. Namely, a drug comprising, as the active ingredient, a proliferative vector which contains a Survivin promoter proliferating depending on the expression of Survivin. The drug may be used in order to treat tumor. In this drug, use may be made of an adenovirus as the vector. In the adenovirus of this drug, an endogenous promoter of an E1A domain may be substituted with a Survivin promoter.

4 Claims, 15 Drawing Sheets

| name of primer | DNA sequence |
|---|---|
| S-E1A (SEQ ID No.3) | 5'-TCAGTCGCATGCGCGGCCGCTACGTAAGCGCGTTACCCGGTGAGTTCCTCAAGAGGC-3'<br>Stuffer \| SphI \| NotI \| SnaBI \| MluI \| Ad5 474~497 |
| AS-E1A (SEQ ID No.4) | 5'-GGACGTCCTAGGGTCGACGCCCCATTTAACACGCCATGCAAG-3'<br>Stuffer \| AvrII \| SalI \| Ad5 1635~1658 (AS) |
| S-E1B19K (SEQ ID No.5) | 5'-TCAGTCCCTAGGGTCGACCATATGGATATCCAAATTGCGTGGGCTAATCTTGGTTACATCT-3'<br>Stuffer \| AvrII \| SalI \| NdeI \| EcoRV \| MfeI \| Ad5 1684~1707 |
| AS-E1B19K (SEQ ID No.6) | 5'-GGACGTGGATCCGCGTCTCAGTTCTGGATACAGTTC-3'<br>Stuffer \| BamHI \| Ad5 2262~2285 (AS) |
| S-BGHpA (SEQ ID No.7) | 5'-TCAGTCGGATCCGCATGCTAGAGCTCGCTGATC-3'<br>Stuffer \| BamHI \| pRc/RSV 693~716 |
| AS-BGHpA (SEQ ID No.8) | 5'-GGACGTGAATTCATAACTTCGTATAATGTATGCTATATGAGGTAATTCAGAAGCCATAGAGCCCACGGCA-3'<br>Stuffer \| EcoRI \| LoxH (AS) \| pRc/RSV 933~956 (AS) |

<PCR condition> thermal denaturation 94 °C, 30 seconds
annealing 57 °C, 30 seconds } 30 cycles
elongation reaction 74 °C, 30 seconds

FIG. 1

| name of primer | DNA sequence |
|---|---|
| S-CMVp<br>(SEQ ID No.9) | 5'-TCAGTCGTCGACCGTTGACATTGATTATTGAC-3'<br>Stuffer \| SalI \| pRc/CMV 231~250 |
| AS-CMVp<br>(SEQ ID No.10) | 5'-GGACGTCAATTGGCTTGGGTCTCCCTATAGTG-3'<br>Stuffer \| MfeI \| pRc/CMV 874~893 (AS) |
| | <PCR condition> thermal denaturation 94 ℃、30 seconds ⎤<br>annealing 57 ℃、30 seconds ⎬ 30 cycles<br>elongation reaction 74 ℃、30 seconds ⎦ |

FIG. 2

DRUG COMPRISING AS THE ACTIVE INGREDIENT PROLIFERATIVE VECTOR CONTAINING SURVIVIN PROMOTER

CROSS-REFERENCE TO RELATED APPLICATIONS

This application is a continuation of application Ser. No. 11/569,625 filed on Nov. 27, 2006, now U.S. Pat. No. 8,142,770, which was the National Stage of International Application No. PCT/JP2005/009819 filed on May 23, 2005, which claims the benefit of Japanese Application Serial No. 2004-154431 filed on May 25, 2004. The contents of all the foregoing applications are hereby incorporated by reference in their entirety.

TECHNICAL FIELD

The invention relates to a pharmaceutical composition containing a survivin promoter and having as an effective ingredient a proliferative vector that heals malignant tumor, and so on by proliferation depending on the expression of survivin.

BACKGROUND ART

Cancers as malignant tumor hold the first place of the cause of death in Japanese, and there has been no decisive therapeutic method for completely curing the cancer. Novel therapeutic methods specifically targeting the cancer have been expected not only from the view point of high therapeutic effects but also from the view point of alleviating side effects. Therefore, developments of gene therapy aiming to specifically target the cancer have been particularly desired. While there are various methods for targeting the cancer and tumor, there are many cases where molecules that are highly expressed only in cancer and tumor cells are utilized by some means. Such tumor specific molecules that are specifically expressed in cancer cells such as tumor markers have been reported. Ideal molecules for this purpose are such molecules as are expressed in the cancer cell as strongly as possible and as are scarcely expressed in normal cells.

Most of the vectors for introducing genes used in the gene therapy of the cancer today are non-proliferative vectors that are genetically modified so that viruses are not proliferated only by introducing the therapeutic vectors after virus infection for securing safety. However, there is a problem that it is natural that the gene cannot be introduced to sections which a virus solution cannot reach by some physical reasons so long as the vector is a non-proliferative type in the case where the vector is administered in vivo in actual clinical treatments, even when the vector itself has an ability for exhibiting a high gene-introducing efficiency. When gene therapy is applied to the cancer using the non-proliferative vector, it is impossible to introduce the genes in all the cancer cells in the body, even though vectors having so excellent gene-introducing efficiency are used in in-vitro experiments.

In other words, the currently used gene therapy using the non-proliferative vector involves such a large restriction that another therapeutic gene that can give some effect to the cells in which the gene is not introduced must be used. However, even in such a case it is impossible to kill all the cancer cells, or only the cancer cells, so that the therapeutic effect of the gene therapy is quite restricted. Accordingly, a perfect cure of the cancer by gene therapy is difficult to attain unless a quite large problem that the cancer recurs from the cancer cells in which the genes are not introduced is not conquered.

Accordingly, virus vectors that proliferate only in the cancer are reported as the vectors for conquering the above-mentioned problem. In a method, a virus gene necessary for proliferation of a virus vector has been attempted to be expressed with a promoter of a cancer specific molecule in order to control the vector so that the virus proliferates in the cancer cell and does not proliferate in normal cells (Rodruguez, R., et. Cancer Res, 57, 2559-2563, 1997). However, specificity for targeting only the cancer as well as the promoter activity was insufficient yet, and developments of the proliferative vectors that are decisively effective have not been successful yet.

Under these situations, survivin was reported as one of novel proteins as a member of inhibitors of apoptosis (IAP) gene family. Survivin is greatly characterized in cancer-specific expression with no expression in differentiated normal tissues (Ambrosini, G. et al., Nat. Med. 3, 917-921, 1997). Expression of survivin is the largest at G2/M stage as a mitotic stage of the cell, and is suppressed in the cell in a non-mitotic resting stage (Li, F, et al.; Nature, 396, 580-584, 1998). A survivin promoter that regulates expression of the survivin gene has an activity for cancer-specific expression (Bao, R. et al.; J. Natl. Cancer Inst. 194, 522-528, 2002), and is considered to have substantially no expression activity of almost all the genes in the normal cell. Accordingly, while it is expected that pharmaceutical compositions for targeting and killing the cancer cells can be developed by cancer cell-specific expression of various genes for cancer therapy, pharmaceutical compositions having as an effective ingredient the proliferative vector containing the survivin promoter have not been proposed yet.

DISCLOSURE OF INVENTION

A gist of the invention is to provide a pharmaceutical composition comprising as an effective ingredient a proliferative vector containing a survivin promoter that proliferates depending on the expression of survivin. The pharmaceutical composition can be used for the therapy of tumors. Adenovirus may be used as vector. Adenovirus is able to substitute an endogenous vector in an EIA region with a survivin promoter, and permits an Rb protein binding sequence to be deleted in the EIA region. Adenovirus is also able to substitute the endogenous promoter in the E1A region with the survivin promoter. Furthermore, adenovirus permits a protein coding region of the EIB region to serve as a 19 KDa protein coding region and/or 55 KDa protein coding region.

Another gist of the invention is to provide a therapeutic method of diseases for allowing survivin to be expressed in high level by using a pharmaceutical composition comprising as an effective ingredient a proliferative vector containing a survivin promoter that proliferates depending on the expression of survivin. This therapeutic method may be used as a gene therapy. The diseases in which survivin is allowed to be expressed in high level include malignant tumors, benign tumors and articular rheumatism. The gist of the invention is to provide a therapeutic method for malignant tumors or benign tumors using any one of the above-mentioned pharmaceutical compositions.

Another gist of the invention is to provide a therapeutic method of diseases for allowing survivin to be expressed in high level by using a pharmaceutical composition comprising introduced therapeutic genes in a proliferative vector including a survivin promoter that proliferates depending on the expression of survivin. The therapeutic gene may be a suicide gene or an apoptosis-inducing gene.

The survivin promoter is not necessarily restricted to human survivin, and other survivin promoters such as simian, mouse and rat survivin promoters may be used.

The proliferative vector containing the survivin promoter can express a gene required for proliferation a virus under the control of the survivin promoter. For example, the virus include adenovirus in which the endogenous promoter in the E1A region or endogenous promoter in the E1B region is substituted with the survivin promoter, adeno-associated viruses in which the endogenous promoters (p5 promoters) of Rep78 and Rep68 or endogenous promoters (p19 promoters) of Rep52 and Rep40 are substituted with the survivin promoter, simplex herpes virus in which the endogenous promoters of early stage expression genes such as ICPO, 4, 22 and 27 protein genes or promoters of thymidine kinase gene are substituted with the survivin promoter, and retrovirus and lentivirus in which endogenous genes in LTR are substituted with the survivin promoter. However, the virus is not restricted to the above-mentioned viruses so long as the virus vector is able to express various virus proliferation-related genes in a survivin promoter-dependent manner. For the adenovirus, human adenovirus type 5, human adenovirus type 2 and human adenoviruses of other types as well as adenoviruses of other animal species may be used.

The proliferative vector containing the survivin promoter can be prepared with reference to the following reports. Adenovirus may be generally manipulated according to "Manipulation of Adenovirus Vectors" by Frank, L. Graham, Chapter 11, p109-128 and "Gene Transfer and Expression Protocols", edited by E. J. Murray, Methods in Molecular Biology, Vol. 7, 1991; and adenovirus may be prepared by the method described in "Combination Gene Therapy for Liver Metastases of Colon Carcinoma in vivo" by Chen, S-H et al., Proc. Natl. Acad. Sci. USA, Vol. 92, 2477-2581, 1995. Adenovirus may be also prepared according to the method described in Japanese Patent Application Number (JP-B) No. 2003-283427 (WO 2005/012536 and Japanese Patent Application Laid-Open (JP-A) No. 2005-46101 after the application). Adeno-associated virus may be prepared according to the method described by Lu, Y., Stem Cells Dev. 13(1): 133-45, 2004 and Grimm, D., Methods 28(2): 146-57, 2002. Herpes virus may be prepared according to the methods by Burton, E A. et al., DNA Cell Biol. 21(12), 915-36, 2002; and Burton, E A. Et al., Curr. Opin. Biotechnology, 13(5), 424-8, 2002. Retrovirus may be prepared according to the methods by Kosai, K I. et al, Hum. Gene Ther. 9(9), 1293-301, 1998 and Kay, M A. et al, Hum Gene Ther. 3(6): 641-7, 1992. Lentivirus may be prepared according to the method by Naldini, L., Curr Opin Biotechnology, 9(5): 457-63, 1998. Gene engineering covering plasmids, DNAs, various enzymes, E. coli and culture cells can be performed according to the method described in "Current Protocols in Molecular Biology", edited by F. Ausubel et. al., 1994, John Wiley & Sons, Inc. and "Culture of Animal Cells: A Manual of Basic Technologies", edited by R. Freshney, second edition (1987), Wiley-Liss.

The pharmaceutical composition of the invention can be used as various pharmaceutical preparations such as injection agents by mixing a proliferative vector of the effective ingredient with pharmaceutically acceptable auxiliaries such as a recipient, carrier and solvent. The mode of administration of the pharmaceutical composition of the invention is not particularly restricted, and may be administered, for example, by injection or by using a catheter or balloon catheter.

While the dosage of the pharmaceutical composition of the present invention can be appropriately increased or decreased by taking pathological conditions, age and weight of a recipient into consideration, a dosage of $1 \times 10^{10}$ pfu (plaque forming unit of infectious titer of the virus) is a measure of the dosage that has been confirmed to be safe by a clinical test to the human (Nemunaitis, J., et al., Cancer Res. 2000, 60: 6359-6366). However, the pharmaceutical composition may be safely and effectively used even when the dosage is not more than or not less than $1 \times 10^{10}$ pfu depending on the kinds of the diseases and virus vectors.

The pharmaceutical composition of the invention is used for gene therapy. The vector in the pharmaceutical composition specifically proliferates in abnormal cells and kills them in the diseases or pathological conditions in which survivin is expressed in high level such as tumors (malignant or benign tumors), articular rheumatism (suppression of articular synovial cells), viral hepatitis (suppression of virus infected cells) and suppression of defective tissues (fibrous tissues and granulation tissues) appearing after the damage in the blood vessel and liver, but does not proliferate in normal cells. Accordingly, the pharmaceutical composition of the invention is able to treat these disease and pathological conditions by suppressing side effects from occurring. The pharmaceutical composition of the invention is also able to enhance therapeutic effects by integrating therapeutic genes into these proliferative vectors.

BRIEF DESCRIPTION OF THE DRAWINGS

FIG. 1 shows PCR primers used for preparing plasmid pΔPr.E1A-CMV.19K and a PCR reaction condition.

FIG. 2 shows PCR primers used for preparing plasmid pΔPr.E1A-CMV.19K and a PCR reaction condition.

BEST MODE FOR CARRYING OUT THE INVENTION

Figure 3:
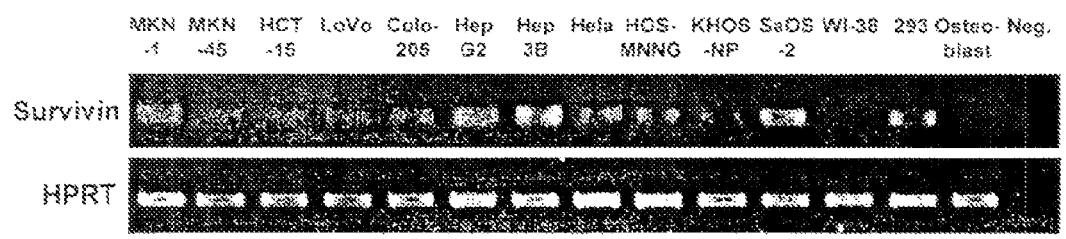
FIG. 3 is a photograph of agarose electrophoresis showing expression of survivin gene in various cancer cells and normal cells; Ost: ostoblast, Neg.: negative control, HPTR: internal control

While the invention is described with reference to examples using adenovirus as the vector, the invention is by no means restricted to these examples. Gene engineering technologies covering plasmids, DNAs, various enzymes, *E coli* and culture cells were applied in the examples according to the methods described in published references unless otherwise stated. General methods of covering of adenovirus and preparation of adenovirus were also applied in the examples according to the methods described in published references unless otherwise stated. Significant differences were calculated by t-test.

EXAMPLE 1

Preparation of Proliferative Adenovirus Containing Survivin Promoter

A part of the liver was isolated from BALB/C mouse, and chromosome DNA was collected using SEPAGENE (trade name, manufactured by Sanko Junyaku Co.). Mouse survivin promoter was cloned by genomic PCR using a primer set specific to mouse survivin promoter using mouse chromosome DNA as a template. Synthesis of sense primer (5'-AGATGGGCGTGGGGCGGGAC-3': SEQ ID No. 1) and antisense primer (5'-TCCGCCAAGACGACTCAAAC-3', SEQ ID No. 2) used was requested to Hokkaido System Science Co. After purification of these primers by electrophoresis, they were inserted into pGEM-T-Easy (manufactured by PROMEGA Co.) of T-vector as a survivin promoter by ligation with T4-DNA ligase (Manufactured by Takara Co.) to obtain pGEM-T-Easy/mSurv.p. The cloned survivin promoter was confirmed to have a proper base sequence with a DNA sequencer. After digesting pGEM-T-Easy/mSurv.p with restriction enzyme SpeI, the product was blunted with T4DNA polymerase. This promoter was digested with NotI in order to cleave the survivin promoter.

Proliferative adenovirus vector Ad.Surv-E1A-CMV-19K/CMV-EGFP (may be referred to Ad.Surv-E1A hereinafter) containing the mouse survivin promoter thus obtained was prepared by the method described in JP-B No. 2003-283427 (WO 2005/012536 and Japanese Patent Application Laid-open (JP-A) No. 2005-46101 after the application) as shown below. In other words, plasmid pSurv.E1A.19K in which expression of E1A gene is controlled by the survivin promoter and expression of E1B19K gene is controlled by the CMV promoter was prepared, and plasmid pSurv.E1A.19K/CMV-EG in which EGFP (enhanced green fluorescent protein) was integrated into the plasmid as a marker was prepared. This plasmid was transfected into 293 cells to prepare Ad.Surv-E1A-CMV-EGFP. This procedure will be described in detail hereinafter.

pΔPr.E1A-CMV.19K was prepared as follows. pHM5 was used as a construction plasmid vector of the adenovirus vector. pHM5 is a cloning vector having recognition sites by SphI, PstI, HineII, XbaI, BamHI, KpnI, Sac I, and EcoRI restriction enzymes, and was provided by Dr. Mark A Kay (Stanford University; details are described in Human Gene Therapy, 10:2013-2017, 1999). Plasmid pXC1 containing human adenovirus genome 5'-side sequence was purchased from Microbix Co. (Toronto, Canada). A region (474 to 1658 bp) containing from an EIA protein coding region of the adenovirus genome to polyadenylation signal without any endogenous promoters, and a region containing only a coding region (1684 to 2285 bp) of E1B 19 KDa protein without any endogenous promoters and polyadenylation signals were amplified using pXCl as templates; and bovine growth hormone polyadenylation signal sequence (BGHp) was amplified using pRc/RSV (manufactured by Invitrogen Co., catalogue No. A-150307) as a template by a PCR method using KOD DNA polymerase (manufactured by Toyobo Co., catalogue No. KOD-l01) with the primer set shown in FIG. 1, and the amplified regions were cloned. Recognition sequences of SphI, NotI, SnaBI and MuII restriction enzymes were added to the sense primer (S-E1A, SEQ ID No. 3) of E1A used herein, and recognition sequences of SalI and AvrII restriction enzymes were added to the antisense primer (AS-E1A, SEQ ID No. 4) of E1A used herein; recognition sequences of AvrII, SalI, NdeI, EcoRV and MfeI restriction enzymes were added to the sense primer (S-E1B19K, SEQ ID No. 5) of E1B (19 KDa), and a recognition sequence of BamHI restriction enzyme was added to the antisense primer (AS-E1B19K, SEQ ID No. 6) of E1B (19 KDa); and a recognition sequence of BamHI restriction enzyme was added to the sense primer (S-BGHpA, SEQ ID No. 7) of BGHpA, and 34 bp LoxH sequence and a recognition sequence of EcoRI restriction enzyme were added to the antisense primer (AS-BGHpA, SEQ ID No. 8). See FIG. 1 for the sequence of each primer and each PCR condition.

Then, the PCR product of the coding region of E1A obtained above and pHM5 were digested with restriction enzymes SphI (manufactured by Takara Co., catalogue No. 1180A) and SalI (manufactured by Toyobo Co., catalogue No. SAL-111), ligated to T4 DNA ligase (manufactured by Takara Co., catalogue No. 6022), and plasmid pΔPr.E1A in which the coding region of E1A is integrated into pHM5 was prepared.

The PCR product containing the coding region of E1B19K obtained above and pΔPr.E1A were digested with restriction enzymes SalI and BamHI (manufactured by Toyobo Co., catalogue No. BAH-111), ligated to T4 DNA ligase, and plasmid pΔPr.E1A-Δr.19KΔpA was prepared. Subsequently, both BGHpA of the PCR product obtained above and pΔPr.ElA-ΔPr.19KΔpA were digested with restriction enzymes BamHI and EcoRI (manufactured by Toyobo Co., catalogue No. ER0271), ligated, and pΔPr.E1AΔ-Pr.19K-BGHpA (BGHpA is omitted hereinafter, and is represented by pΔPr.E1A-ΔPr.19K) was manufactured. For eliminating possible variation of the base sequence as a results of using the PCR method, it was confirmed that the DNA sequence of pΔPr.E1A-ΔPr.19K has a correct sequence as measured with a DNA sequencer (trade name: ABI PRISM 310 GENETIC ANALYZER, manufactured by Applied Biosystems Co.), and that the desired DNA construct was manufactured. The DNAs cloned using the PCR method were always confirmed using the DNA sequencer hereinafter.

PΔPr.E1A-ΔPr.19K thus prepared has a background of pHM5. The plasmid is able to freely insert the promoter at the upstream of DNA from the upstream using recognition sequences of SphI, NotI, SnaBI and MuII restriction enzymes as multi-cloning sites, the coding region of E1A protein, recognition sequences of SalI, NdeI, EcoRV and MfeI restriction enzymes as multi-cloning sites, the coding region of E1B19 KDa protein, and multi-cloning sites of E1A and E1B19 KDa containing BGHpA and LoxH sequences. Since the restriction enzyme sites of SnaBI and EcoRV restriction enzymes that serve as blunt-end fragments are used in the multi-cloning sites at the upstream of E1A and E1B19 kDa, respectively, promoter sequences cleaved with any restriction enzymes may be simply and reliably integrated into PΔPr.E1A-ΔPr.19K by ligation after being processed into blunt-end fragments.

A plasmid was prepared by inserting CMV as a permanently and strongly expressing promoter (Boshart, M. et al., Cell, 41,521-530, 1985; Nelson, J.A., Et al, Mol. Cell. Bol., 7, 4125-4129, 1987) into pΔPr.E1A-ΔPr.19K at the upstream of E1B19K. CMV promoter was amplified by PCR with a sense primer (S-CMVp, SEQ ID No. 9) having a SalI recognition site and an antisense primer (AS-CMVp, SEQ ID No. 10) having an MfeI recognition site using plasmid pRc/CMV (manufactured by Invitrogen Co, catalogue No. 9) as templates (see FIG. 2 for the sequence of each primer and PCR conditions). This PCR product (231 to 893 of pRc/CMV) and pΔPr.E1A-ΔPr.19K were digested with SalI (manufactured by Toyobo Co., catalogue No. SAL-1ll) and MfeI (manufactured by New England Biolabs Co., catalogue No. R0589S), ligated to T4 DNA ligase, and pΔPr.E1A-CMV-19K was prepared by inserting CMV promoter at the upstream of E1B19K.

pΔPr.E1A-CMV.19K was digested with MuII and, after forming blunt-ends with T4DNA polymerase, was digested with NotI. After dephosphorylation with calf intestine alkaline phosphatase (CIP: Calf Intestinal Alkaline Phosphatase manufactured by Takara Co.) for preventing auto-ligation, the survivin promoter obtained above was inserted by ligating with T4 DNA ligase to obtain pSurv.E1A-CMV.19K.

Subsequently, pSurv.E1A-CMV.19K/CMV-EGFP in which EGFP (enhanced green fluorescent protein) was integrated was prepared as follows.

A freely insertable plasmid into pSurv.E1A-CMV.19K was prepared by taking advantage of a Cre recombination reaction. A plasmid having LoxP sequence and being able to be integrated with EGFP and its promoter was prepared at first as follows. Kn (kanamycine) resistant gene of pUni/V5-HisC (manufactured by Invitrogen Co., Carlsbad, Calif., catalogue No. ET003-11) was cleaved with BglII (manufactured by Toyobo Co., catalogue No. BGL-211) and SmaI (manufactured by Toyobo Co., catalogue No. SMA-111), blunted with T4 DNA polymerase, and was subjected to CIP treatment for preventing auto-ligation. After digesting Tc (tetracycline) resistant gene from pBR322 (manufactured by Toyobo Co., catalogue No. DNA-003) with SspI (manufactured by Toyobo Co., catalogue No. SSP-101) and StyI (manufactured by New England Violabs, Inc., Bevery, Mass., catalogue No. R0050S), the product was blunted with T4 DNA polymerase. This product was inserted into pUni/V5-HisC blunted by removing Kn resistant gene as described above by ligation using T4 DNA ligase, and plasmid pUni/V5-HisC-Tc was prepared by substituting Kn resistant gene with Tc resistant gene. This pUni/V5-HisC-Tc was further digested with XhoI, and was blunted with T4 DNA polymerase followed by CIP treatment. On the other hand, the CMV promoter, obtained by PCR with the sense primer (S-CMVp, SEQ ID No. 9) having MfeI site and antisense primer (AS-CMVp, SEQ ID No. 10) having SalI site using plasmid pRc/CMV as a template as described above, was cleaved with SalI and MfeI restriction enzymes. The cleaved product blunted with T4 polymerase was ligated to blunted pUni/V5-HisC-Tc using DNA ligase, and pUni/V5-HisC-Tc-CMV was prepared. pUni/V5-HisC-Tc-CMV is a plasmid prepared by inserting a CMV promoter into pUni/V5-HisC-Tc, and is able to insert desired genes to be expressed at the downstream of the CMV promoter using either AgeI, ApaI or StuI of the multi-cloning site. The CMV promoter and a gene inserted at the downstream of the promoter may be inserted into pSurv.E1A-CMV.19K for regulating above-mentioned E1A.

Subsequently, pEGFP-C1 (manufactured by CLONETECH Co., catalogue No. 6084-1) was digested with BclI and, after forming blunt ends with T4 polymerase, cDNA of EGFP was cleaved by digestion with AgeI. On the other hand, pUni/V5-HisC-Tc-CMV was digested with ApaI and, after forming blunt ends with T4 DNA polymerase, further digested with AgeI. The cleaved cDNA fragment of EGFP was inserted by ligation with T4 DNA ligase to obtain pUni/V5-HisC-Tc-CMV-EGFP. pUni/V5-HisC-Tc-CMV-EGFP is an expression vector capable of expressing EGFP from the CMV promoter, while CMV-EGFP gene can be inserted into pSurv.E1A-CMV.19K for controlling E1A with survivin by a Cre recombination reaction.

pSurv.E1A-CMV.19K and pUni/V5-HisC-Tc-CMV-EGFP can be readily recombined with Cre recombinase (a reaction for linking two plasmids into one plasmid by recognizing LoxP and LocX sequences). pSurv.E1A-CMV-19K and pUni/V5-HisC-Tc-CMV-EGFP (100 ng each) were allowed to react using a Cre recombinase (37° C., 20 minutes). Then, Cre was inactivated by treating at 65° C. for 5 minutes in order to stop the reaction. This reaction solution was transformed into competent cells DH5α (manufactured by Toyobo Co., catalogue No. DNA-903), and the cells were cultivated on LB (Luria-Bertani, purchased from Nacalai Tesque Co., catalogue No. 20066-95) agarose plate containing tetracycline (7.5·g/ml, purchased from Wako Pure Chemical Industries, Inc., catalogue No. 205-08591). pSurv.E1A-CMV-19K cannot form colonies due to the Kn resistant gene, while pUni/V5-HisC-Tc-CMV-EGFP cannot also form colonies in DH5α cells since it has a special Ori (*E. coli* replication starting point) named as R6K$^r$. On the other hand, the plasmid prepared by recombination of pSurv.E1A-CMV.19K and pUni/V5-HisC-Tc-CMV-EGFP was able to form colonies since it contains both pCU Ori and Tc$^r$. Cre recombinase was extracted using adenovirus vector AxCANCre (supplied from the DNA bank of RIKEN). HepG2 cells (provided by Medical Cell Resource Center, Institute of Development, Aging and cancer, Tohoku University) as human liver cancer cells having high gene-introducing efficiency with viruses were infected with AxCANCre at 30 MOI (degree of multiple-infection, 1 MOI=1 plaque forming unit/cell) on a culture dish with a diameter of 10 cm; cells were peeled by treating with trypsin (purchased from Nacalai Tesque Co. catalogue No. 35555-54) three days after infection; the cells were lysed with 200 μl of Lysis buffer (20 mM Tris pH 7.5, 150 mM NaCl, 10 mM MgCl$_2$, glycerol 10%, protease inhibitor cocktail (manufactured by Sigma Co., catalogue No. P2714) 1%) after washing with PBS; and Cre recombinase was obtained by repeating freezing and thawing three times. Colonies appeared at the position was subjected to a reaction with Cre recombinase, and all the colonies appeared were positive clones. Plasmid pSurv.E1A-CMV.19K/CMV-EGFP was obtained by this reaction.

pSurv.E1A-CMV.19K/CMV-EGFP obtained above was integrated into 30.3 kb plasmid pAdHM4 (supplied from Dr. Mark A. Kay, Stanford University) containing the adenovirus genome, and pAd.Surv-E1A-CMV-19K/CMV-EGFP was obtained. Plaques of adenovirus were appeared by digesting this pAd.Surv-E1A-CMV-19K/CMV-EGFP with restriction enzyme Pad followed by transfection with 293 cells. The plaque was collected, and genes were amplified by infecting into 293 cells. Subsequently the plaque was concentrated by concentration-gradient centrifugation with cesium chloride, and was purified with a desalting column (manufactured by Biolad Co.). Proliferative adenovirus vector Ad.Surv-E1A-CMV-19K/CMV-EGFP was thus obtained.

EXAMPLE 2

Expression of Survivin in Various Cancer Cells and Normal Cells

Expression of survivin in various cancer cells was confirmed by RT-PCR. After recovering various cancer cells (MKN-1, MKN-28, MKN-45, HCT-15, LoVo, Colo-205, Hep-G2, Hep-3B, Hela, HOS-MNNG, KHOS-NP and SaOs-2) by treating with trypsin (purchased from Nacalai Tesque Co.), the cells were homogenized by adding 1 ml of SEPASOL RNA I Super (purchased from Nacalai Tesque Co., catalogue No. 304-86). The homogenate solution was separated into an aqueous phase by adding phenol and chloroform, and RNA was allowed to precipitate from the aqueous phase by adding isopropanol.

After centrifugation, RNA was suspended by adding 70% ethanol, and was extracted by centrifugation again. Total RNA (1 μg) was reverse-transcripted using Superscript II reverse transcriptase (trade name, manufactured by Invitrogen Co.) to obtain complementary DNA (cDNA). The same procedure was applied to WI-38 of normal cells, OST of human primary culture ostoblast (purchased from Sanko Junyaku Co.) and 293 cells as a positive control.

Synthesis of sense primer (5'-GCATGGGTGC-CCCGACGTTG-3'; SEQ ID No. II) and antisense primer (5'-GCTCCGGCCAGAGGCCTCAA-3', SEQ ID No. 12; Kajiwara Y., et al.; Cancer 97, 1077-1083, 2003) of survivin used was requested to Hokkaido System Science Co. Hypoxanthine phosphoribosyl transferase (HPRT) was used as an internal control. Promega Taq (trade name, manufactured by Promega Co., catalogue No. M1865) was used for PCR, wherein the PCR condition was heat denaturation at 94° C. for 30 seconds, annealing at 56° C. for 1 minute and elongation reaction at 72° C. for 1 minute, and this procedure was repeated 40 cycles. The HPRT condition was annealing at 57° C. and 35 cycles. T3 Thermocucler (trade name, manufactured by Biometra Co.) was used as a PCR thermal cycler. As shown in FIG. 3, while the strength of expression was different among the cancer cells such as strong expression in liver cancer cells (Hep-G2, Hep-3B) and weak expression in large intestine cancer, expression was observed in wide ranges of cancer cells. Slight expression was observed in normal cells WII-38 and human primary culture ostoblast cells OST (purchased from Sanko Junyaku Co.).

EXAMPLE 3

Expression of TERT Gene in Various Cancer Cells and Normal Cells

Expression of TERT in various cancer cells was confirmed by RT-PCR. After recovering various cancer cells (MKN-1, MKN-28, MKN-45, HCT-15, LoVo, Colo-205, Hep-G2, Hep-3B, Hela, HOS-MNNG, KHOS-NP and SaOs-2) by treating with trypsin (purchased from Nacalai Tesque Co.), the cells were homogenized by adding 1 ml of SEPASOL RNA I SUPER (purchased from Nacarai Tesque Co., catalogue No. 304-86). The homogenate solution was separated into an aqueous phase by adding phenol and chloroform, and RNA was allowed to precipitate from the aqueous phase by adding isopropanol. After centrifugation, the precipitate was suspended in 70% ethanol, and RNA was extracted by centrifugation again. 1 μg of total RNA was reverse-transcripted using SuperScript II reverse transcriptase (trade name, manufactured by Invitrogen Co.) to obtain complimentary DNA (cDNA). The same procedure was applied to WI-38 of normal cells and Ostec-blast of human primary culture ostoblast (purchased from Sanko Junyaku Co.).

Figure 4:
FIG. 4 is a photograph showing expression of TERT gene in various cancer cells and normal cells; Osteo-blast: ostoblast, Neg.: negative control, HPTR: internal control

Synthesis of sense primer (5'-TTCCTGCACTGGCTGAT-GAGTGT-3'; SEQ ID No. 13) and antisense primer (5'-CGCTCGGCCCTCTTTTCTCTG-3', SEQ ID No. 14; Yan P. et al.; Cancer Res, 59, 3166-3170) of TERT used was requested to Hokkaido System Science Co. Hypoxanthine phosphoribosyl transferase (HPRT) was used as an internal control. Promega Taq (trade name, manufactured by Promega Co., catalogue No. M1865) was used for PCR, wherein the PCR condition was heat denaturation at 94° C. for 30 seconds, annealing at 59° C. for 1 minute and elongation reaction at 72° C. for 1 minute, and this procedure was repeated 36 cycles. The HPRT condition was annealing at 57° C. and 35 cycles. T3 Thermocucler (trade name, manufactured by Biometra Co.) was used as a PCR thermal cycler. As shown in FIG. 4, while the strength of expression was different among the cancer cells, expression was observed in wide area of the total cancer cells. No expression was observed in normal cells WII-38 and human primary culture ostoblast cells (purchased from Sanko Junyaku Co.).

EXAMPLE 4

Activity of Survivin Promoter

Ad.Surv-LacZ in which Mouse survivin promoter cloned as described above was integrated was prepared and purified. Ad.CMV-LacZ and Ad.RSV-LacZ were used as references. Various cancer cells were cultivated on 6 well plates at a density of 5×10$^5$ cells/well, and the culture cells were infected with Ad.CMV-LacZ, Ad.RSV-LacZ and Ad.SurvLacZ, respectively, at MOI 30 (multiplicity of infection, 1 MOI=1 plaque forming unit/cell) on the next day of cultivation.

Figure 5:
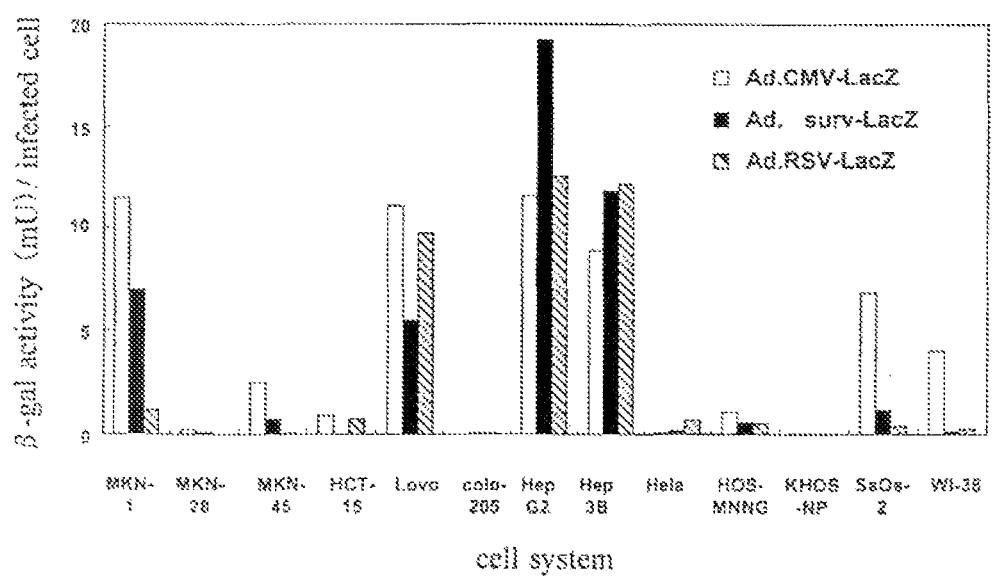
FIG. 5 shows the result of comparison of the activity of mouse survivin promoter with RSV and CMV promoters in various cancer cells and normal cells. RSV promoter is a non-specific promoter having an activity in all cells).

On the day next, the protein was recovered, and was subjected to β-galactosidase assay using 10 μg of proteins. The results are shown in FIG. 5. As a whole, it was shown that the activity of the survivin promoter is stronger than the activities of CMV and RSV promoters. While Hep-G2 and Hep-3B in which survivin is strongly expressed showed strong promoter activities in each observation, expression of the survivin gene by RT-PCR was not always correlated with the strength of the activity of the promoter. Ad.CMV-LacZ was provided by Dr. Zong Sheng Guo, Department of Surgery and Cancer Institute, University of Pittsburgh (prepared as described in Gene Ther, 1996; 3 (9): 802-810). Ad.RSV-LacZ was prepared as follows. The lacZ coding region was cleaved by digestion of plasmid pMV-LacZ (provided by Dr. Gretchen Darlington, Baylor College of Medicine) with restriction enzyme NotI, and pAd.RSV-LacZ was obtained by ligation with plasmid pAdL.2/RSV/hPAH (provided by Dr. Zong Shebg Guo) digested with restriction enzyme NotI. Ad.Surv-LacZ was further prepared as follows. Blunted pHM-ΔPr.6, prepared by removing the CMV promoter from plasmid pHM-CMV6 (provided by Dr. Mark A Kay) by cleaving with restriction enzyme MunI/NheI, was ligated to the blunted survivin promoter prepared by cleaving with pGEM-T-Easy to obtain pHM-Surv.p, which was ligated to the LacZ gene cleaved from pAd.RSV-LacZ with restriction enzyme NotI, and pHM-Surv-LacZ was obtained. pHMSurv-LacZ was digested with I-Ceu/PI-SceI, and ligated to pAd.HM4 digested with I-Ceu/PI-SceI to obtain pAd.HM4-Surv-LacZ. Ad.Surv-LacZ was obtained by transfection of 293 cells with pAd.HM4-Surv-LacZ.

EXAMPLE 5

Figure 6:
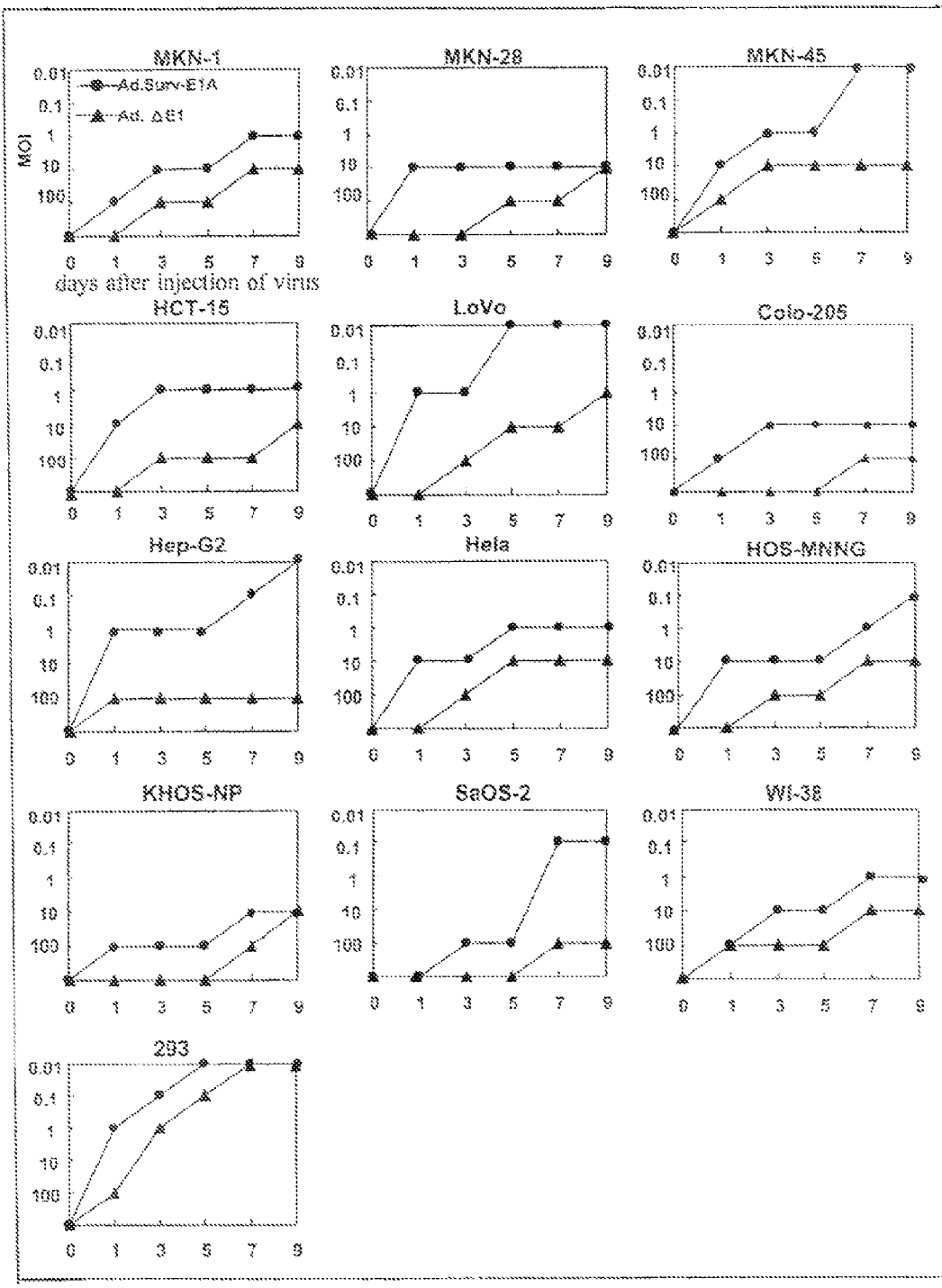
FIG. 6 shows graphs of monitoring of EGFP positive ratios using proliferative adenovirus vector in various cancer cells and Norman cells as indices. The horizontal axis shows the days after infection while the vertical axis shows MOI, and the points when EGFP is 100% are plotted in each graph.
Figure 7:
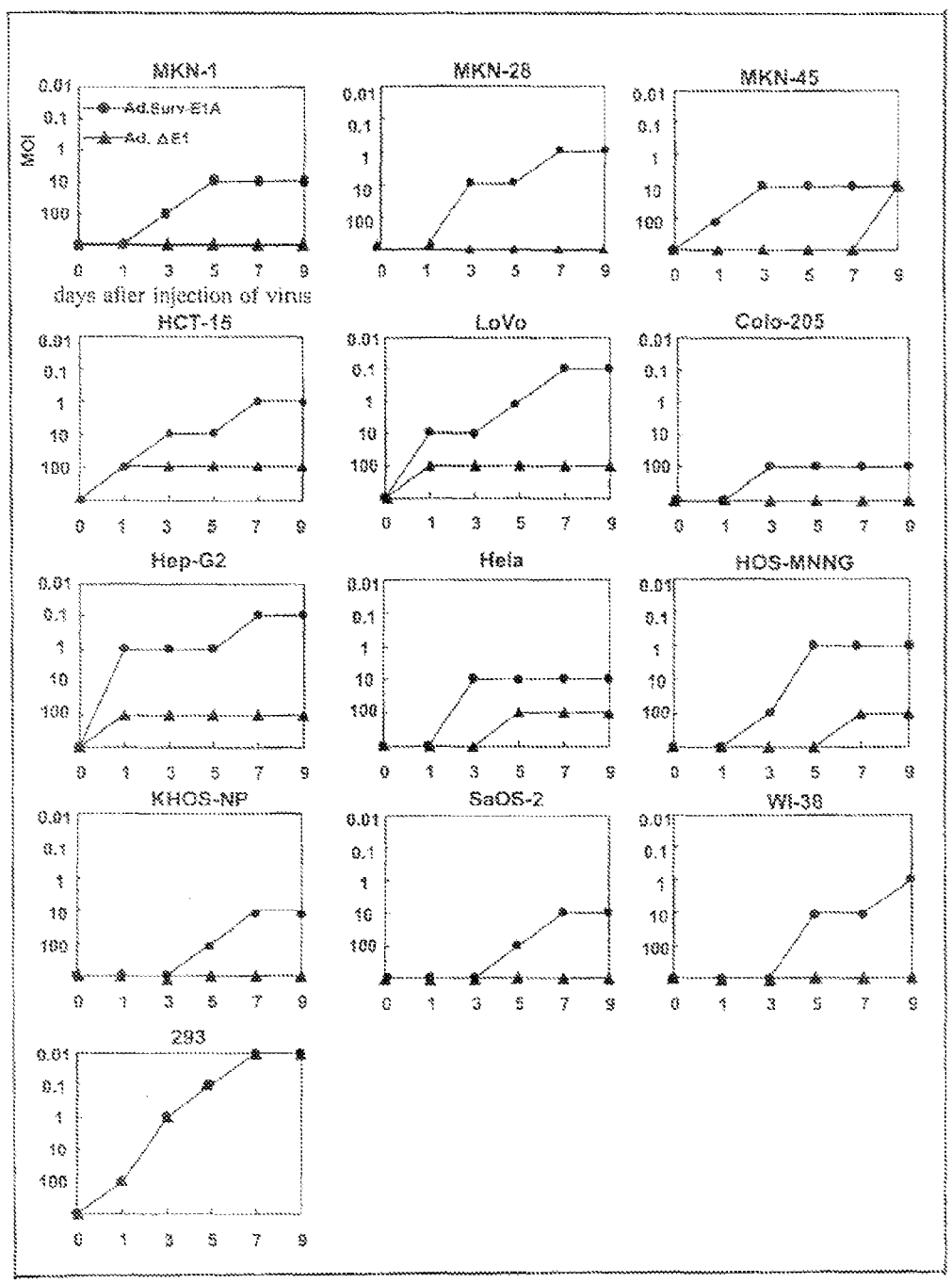
FIG. 7 shows graphs of monitoring of emergence of CPE using proliferative adenovirus vector in various cancer cells and normal cells as indices. The horizontal axis shows the days after infection while the vertical axis shows MOI, the points when CPE is 100% are plotted in each graph.

Analysis of Proliferating Ability of Proliferative Adenovirus Vector Containing Survivin Promoter in Various Cancer Cells Various cancer cells were cultivated on 24 well plates at a density of $8 \times 10^4$ cells/well, and the culture cells were infected with Ad.Surv-E1A-CMV-19K/CMV-EGFP (Ad.Surv-E1A) as a proliferative cell and Ad.ΔE1-GFP (may be referred to Ad.ΔE1 hereinafter) as a reference that is E1 deleted non-proliferative ADV at MOIs of 0, 0.01, 0.1, 1, 10 and 100, respectively, on the next day of cultivation. Proliferation ability of proliferative adenovirus was monitored with time from the next day of infection by the emergence of cell damage (CPE) by observation of the EGFP positive ratio under a fluorescence microscope. The results are shown in FIGS. 6 and 7. Proliferation of Ad.Surv-E1A was evident in all the cancer cells as compared with that of Ad.ΔE1. In the groups infected with Ad.Surv-E1A, the EGFP positive ratio was 100% in MOI 100 group, and the EGFP positive ratio was also 100% in all the cancer cells in MOI 10 group except KHOS-NP and SaOs-2. Since CPE is observed in all the cancer cells at MOI 100 at day 3 after the infection except KHOS-NP and SaOs-2, both results showed good correlation to one another. Both the positive ratios of EGFP and CPE were also enhanced, although the strength is different with time. Since proliferation of proliferative adenovirus observed with marker gene EGFP and CPE representing the damage of the cell emerged in correlation to one another, it was proved that Ad.Surv-E1A proliferates in the survivin expression cells, and kills the cell by toxicity of Ad.Surv-E1A. Ad.ΔE1GFP was prepared as follows. Plasmid pHM-CMV6 (supplied from Dr. Mark A. Kay) was digested with restriction enzyme XbaI and blunted, and then digested with restriction enzyme NheI. EGFP was prepared by digesting pEGFP-C1 (manufactured by CLONTECH Co., Palo Alto, Calif.) with restriction enzyme BclI, blunted, and digested and cleaved with restriction enzyme NheI. This EGFP was ligated to the digested and blunted plasmid pHM-CMV6 prepared as described above, and pHM-CMV-EGFP was obtained. This pHM-CMV-EGFP was digested with I-Ceu/PI-SceI, and ligated to pAd-HM4 digested with I-Ceu/PI-SceI to obtain pAd.HM4-CMV-EGFP, which was transfected into 293 cells to obtain Ad.ΔE1-GFP.

Figure 8:
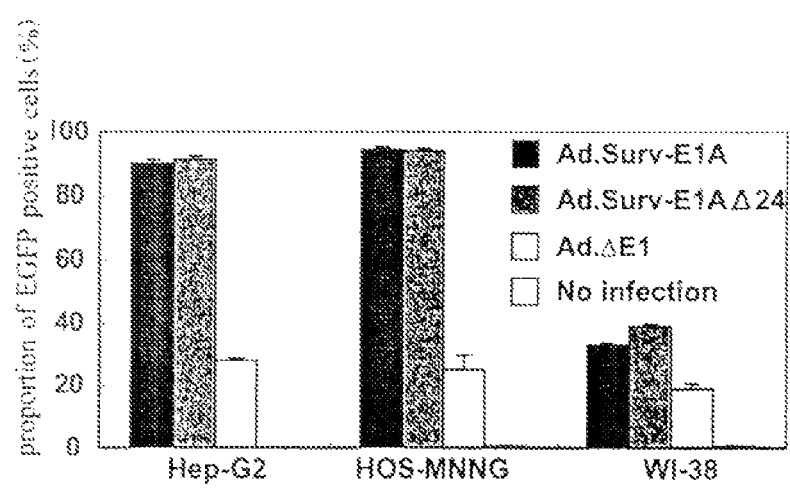
FIG. 8 shows a graph of EGFP positive ratios analyzed by flow cytometry after infecting various cells with Ad.Surv-E1A (proliferative vector), Ad.Surv-E1AΔ24 (proliferative vector) and Ad.ΔE1 (non-proliferative vector).

The proportion of the EGFP positive cells was quantitatively evaluated by flow cytometry analysis. Hep-G2, HOS-MNNG and WI-38 were cultivated on culture dishes with a diameter of 10 cm, and the cultured cells were infected with Ad.Surv-IA (proliferative vector), Ad.Surv-EIAΔ24 (proliferative vector) and Ad.ΔE1 (non-proliferative vector), respectively, at MOI 0.1 (Hep-G2) and MOI 1 (HOS-MNNG and WI-38) on the next day of cultivation. Each cell strain was recovered 24 hours after the infection, recovered cells were fixed with 4% paraformaldehyde, and the EGFP positive ratio was measured with a flow cytometer (Trade name: FACSCalibur with CELLQuest software, manufactured by Becton Dickinson Co.). As shown in FIG. 8, although the EGFP positive ratio was almost identical in Ad.ΔE1 infection group of various cells (or the introduction efficiency is almost identical), Hep-G2 and HOS-MNNG of the cancer cells showed 90% or more of the EGFP positive ratio in the Ad.Surv-E1A and Ad.Surv-E1AΔ24 infection groups while the EGFP positive ratio in WI-38 of the normal cells was remarkably suppressed. This shows that Ad.Surv-E1A and Ad.Surv.E1AΔ24 have high tumor specificity. No significant difference was observed in the tumor specificity between Ad.Surv-E1A and Ad.Surv.E1AΔ24. Ad.Surv.E1AΔ24 deficient in the Rb protein bonding sequence was prepared according to the method described in JP-B No. 2003-283427 (WO 2005/012536 and JP-A No. 200S-46101 after application).

Figure 9:
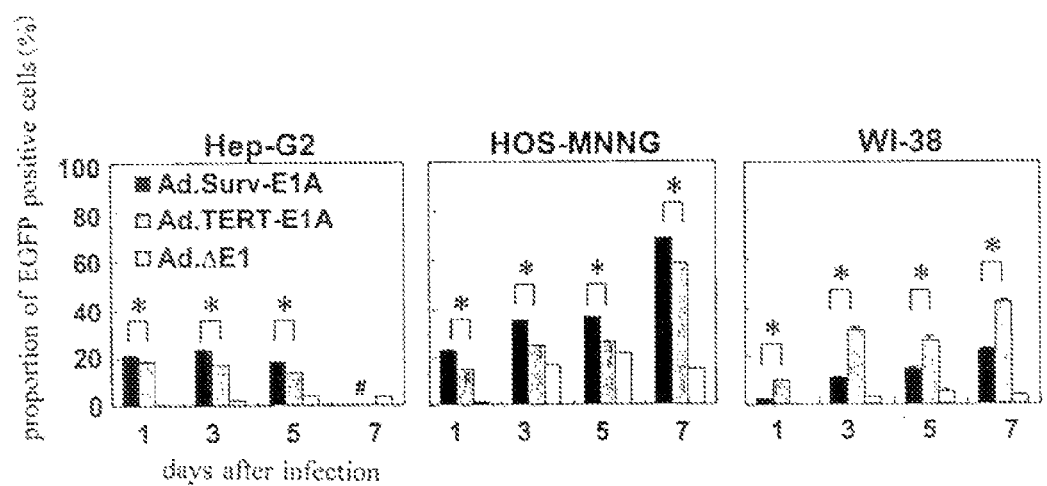
FIG. 9 shows graphs of EGFP positive ratios analyzed by flow cytometry after infecting various cells with Ad.Surv-E1A, Ad.TERT-E1A and Ad.ΔE1. *P<0.05; # shows the infected cell is CPE, and measurements were impossible due to peeling of the cell from the culture dish.

The same above-mentioned cells were infected with Ad.Surv-E1A, Ad.TERT-E1A and Ad.ΔE1, and the proportion of the EGFP positive cells was quantitatively evaluated by the analysis with the flow cytometer. MOIs were 0.03 in Hep-G2 and 0.1 in HOS-MNNG and WI-38, and the cells were recovered 1, 3, 5 and 7 days after the infection and were measured as described above. As shown in FIG. 9, Hep-G2, HOS-MNNG and Ad.Suev-E1A of the cancer cells were more efficiently proliferated than Ad.TERT-E1A throughout the measuring time period, and proliferation of Ad.Surv-E1A was suppressed in WI-38 of the normal cells. This shows that Ad.Surv-E1A shows high tumor specificity. The preparation method of Ad.TERT-E1A will be described hereinafter.

EXAMPLE 6

Figure 10:
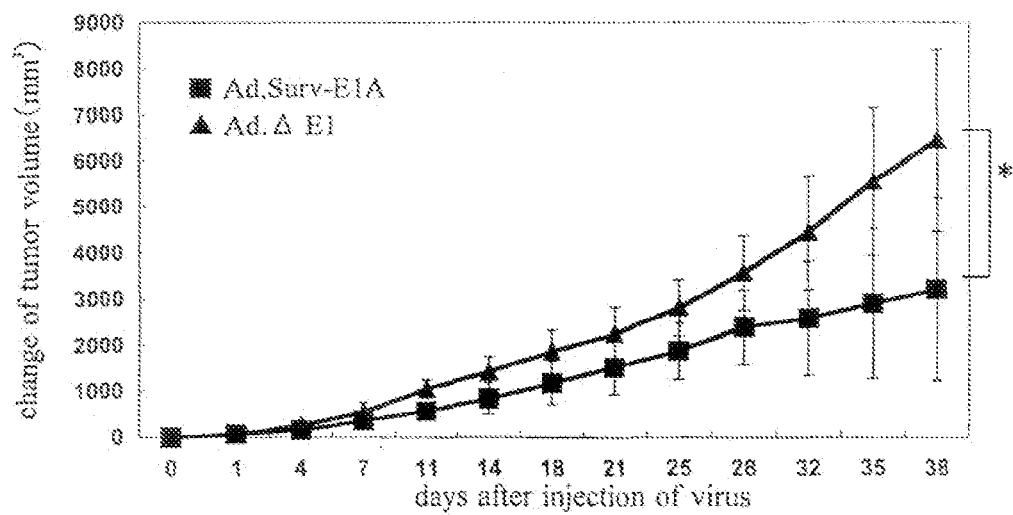
FIG. 10 is a graph showing the changes of the volume of the tumor after injecting Ad.Surv-E1A and Ad.ΔE1 into respective tumors.

Anti-Tumor Effect of Proliferative Adenovirus Containing Survivin Promoter In Vivo Nude mouse was used for the experimental animal for confirming the anti-tumor effect of proliferative adenovirus in vitro. HOS-MNNG of human osteosarcoma cell strain ($5 \times 10^6$) was subcutaneously injected at the back of the nude mouse of age 5 week, and $1 \times 10^8$ pfu of Ad.Surv-E1A (n=8) and Ad.ΔE1 (n=9) were injected into the tumor only once, respectively. The diameter of the tumor was periodically measured from the next day, and changes of the tumor volume (the tumor volume was calculated by major axis diameter×minor axis diameter×minor axis diameter/2) were compared for each group. The results are shown in FIG. 10. Proliferation of the tumor was significantly suppressed (p<0.005 38 days after injection of the virus) in the Ad.Surv-EIA administration group as compared with the Ad.ΔE1 administration group as the control in 11 to 18 days and 28 to 38 days after injection of the virus. These results show usefulness of the proliferative adenovirus vector containing the survivin promoter in the cancer gene therapy.

Figure 11:
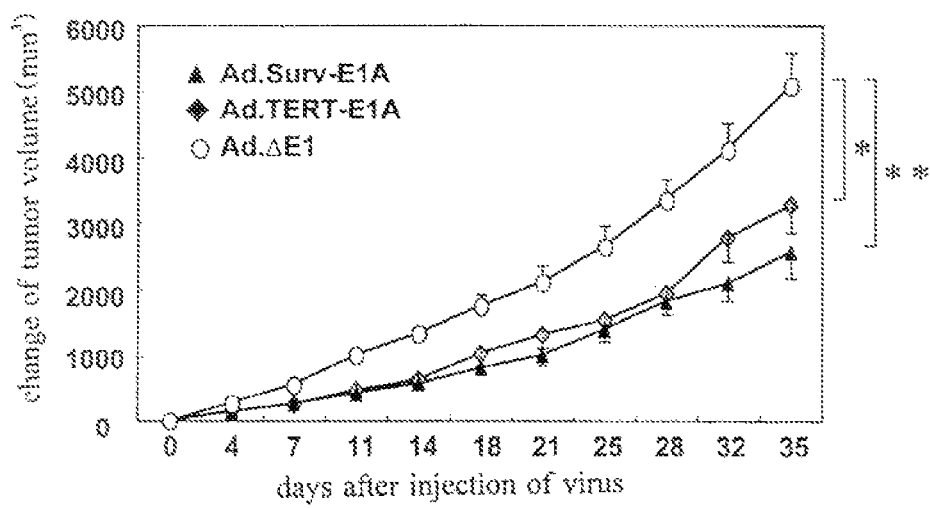
FIG. 11 is a graph showing the changes of the volume of the tumor after injecting Ad.Surv-E1A, Ad.TERT-E1A and Ad.ΔE1 into respective tumors. *P<0.05 and **P<0.005 correspond to Ad.ΔE1.

The cells were also infected with Ad.Surv-E1A and Ad.TERT-E1A by the same above-mentioned experiments (Ad.Surv-E1A: n=8, Ad.TERT-E1A: n=9, Ad.ΔE1: n=11). As shown in FIG. 11, both Ad.Surv-E1A and Ad.TERT-E1A significantly suppressed proliferation of the tumor as compared with Ad.ΔE1. While no significant difference was observed between Ad.Surv-E1A and Ad.TERT-E1A, the p-value of Ad.Surv-E1A was smaller than the value of Ad.ΔE1 as the control, and shows that the therapeutic effect is higher in Ad.Surv-E1A than in Ad.TERT-E1A. The preparation method of Ad.TERT-E1A will be described hereinafter.

EXAMPLE 7

Figure 12:
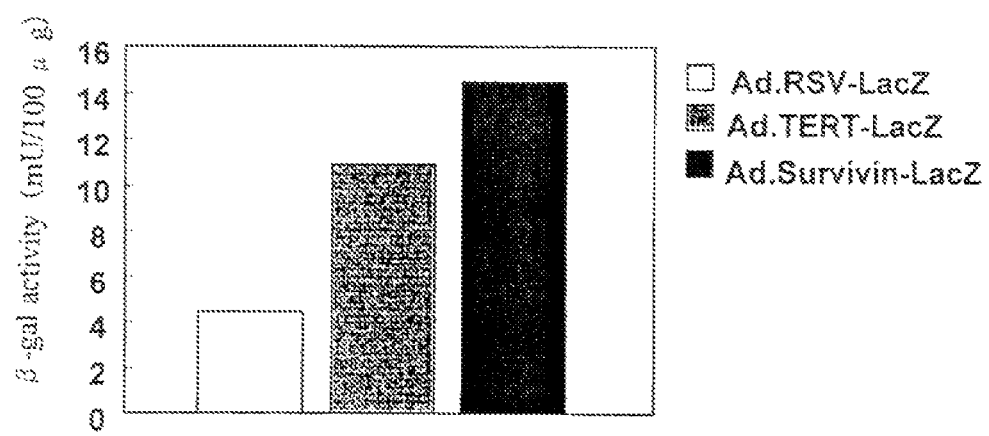
FIG. 12 is a graph showing comparison of activities of survivin promoter, RSV promoter and TERT (telomerase reverse transcriptase) promoter.

Comparison of Activities Among Survivin Promoter, RSV (Rous Sarcoma Virus) Promoter and Tert (Telomerase Reverse Transcriptase) Promoter Hela (human cervical cancer) cells ($5 \times 10^5$ cells each) were cultivated, and were infected with Ad.RSV-LacZ, Ad-TERT-LacZ and Ad.Survivin-LacZ, respectively, at MOI 30 24 hours after cultivation. The cells were recovered 24 hours after the infection, and absorbance at 420 nm was measured by allowing the cell extraction solutions and X-gal substrate (manufactured by PROMEGA Co., Madison, Wis.) to react for 30 minutes in order to obtain the β-galactosidase activity or the promoter activity. The results are shown in FIG. 12. The survivin promoter showed the highest activity among the three promoters. This result shows that the survivin promoter is excellent in tumor specificity as well as in the strength of the promoter as compared with the tumor specific TERT promoter that has been reported (Takamura, M. et al., Cancer Res., 59(3): 551-7, 1999). Ad.TERT-LacZ was prepared as follows. The blunted TERT promoter, which was cleaved from plasmid pGL3-181 (supplied from Mr. Kyo Tohru, clinic of gynecology and obstetrics, Kanazawa University) containing the TERT promoter by digesting with restriction enzymes MluI and BglII, was ligated to blunted pHM-ΔPr.6 prepared by removing the CMV promoter from plasmid pHM-CMV6 (supplied from Dr. Mark A Kay) by cleaving with restriction enzymes MunI/NheI, and pHMTERT.p was obtained. pHM-TERT-lacZ was obtained by ligating LacZ gene, which was cleaved from pAd.RSV-LacZ with restriction enzyme NotI, to pHM-TERT.p.pAd.HM4-TERT-LacZ was obtained by digesting pHM-TERT-lacZ with restriction enzymes I-CeuI/PI-SceI, and by ligating digested pHM-TERT-lacZ to pAd.HM4 that was also digested with the same restriction enzymes I-CeuI/PI-SceI. Ad.TERT-lacZ was obtained by transfection of pAd.HM4-TERT-LacZ into 293 cells.

Figure 13:
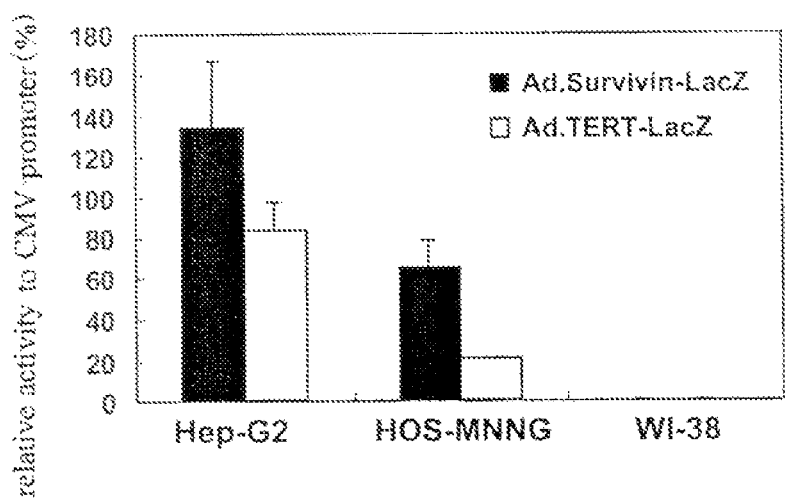
FIG. 13 is a graph plotting the activities of survivin promoter and TERT promoter in various cells calculated as the ratios against the CMV promoter activity. The vertical axis shows the activity ratio of promoters.

Each cells of Hep-G2, HOS-MNNG and WI-38 were infected with Ad.Survivin-LacZ, Ad.TERT-LacZ and Ad.CMV-LacZ by the same method as the method for infecting Hela (human cervical cancer) cells, and activities of respective promoters were compared. In FIG. 13, the activities of the survivin promoter and TERT promoter in each cell were calculated as ratios against the CMV promoter activity, and the ratio were compared to one another.

The results showed that, while both of the survivin promoter and TERT promoter have no activities in normal cells WI-38, the survivin promoter showed a stronger activity than the TERT promoter in both cancer cells Hep-62 and HOS-MNNG. In other words, the survivin promoter is superior to the TERT promoter in both tumor specificity and strength of the promoter.

EXAMPLE 8

Figure 14:
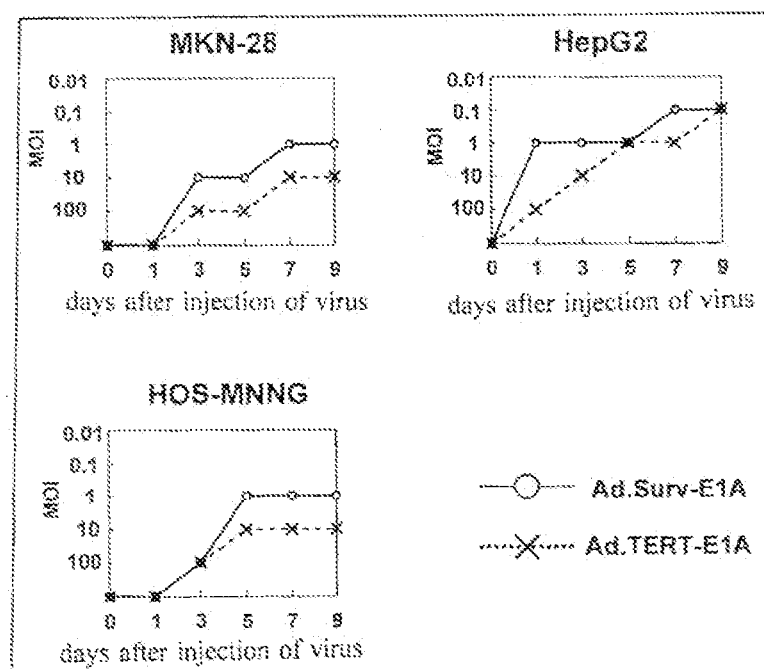
FIG. 14 shows the graphs of comparison of proliferating ability between proliferative adenovirus containing TERT promoter and proliferative adenovirus containing survivin promoter.

Comparison of Proliferative Ability Between Proliferative Adenovirus Containing TERT Promoter and Proliferative Adenovirus Containing Survivin Promoter MKN-28 (human stomach cancer cells), HepG2 (human liver cancer cells) and HOS-MNNG (human osteosarcoma cells) were infected with Ad.TERT-E1A-CMV-19K/CMV-EGFP (referred to Ad.TERT-E1A; TERT dependent proliferative adenovirus hereinafter) Ad.Surv-E1A at various concentrations, and death of the cells induced by the adenovirus was observed. The results are shown in FIG. 14. It was shown that Ad.Surv-EIA have higher virus proliferating ability (cell death inducing ability) among the proliferative vectors. This shows that the proliferative vector controlled by the survivin promoter is superior to the proliferative virus vector controlled by the TERT promoter as one of the tumor specific promoters reported today (Huang T G et al., Gene Ther. 10(15): 1241-7, 2003; Wirth T et al, Cancer Res. 63(12): 3181-8, 2003). Ad.TERT-E1A can be prepared by the almost same method as preparing Ad.Surv-E1A. pΔPr.E1A-CMV-19K was digested with restriction enzyme MluI, and blunted with T4DNA polymerase. The TERT promoter was cleaved by digesting plasmid pGL3-181 containing TERT promoter (provided by Tohru Kyo, clinic of gynecology and obstetrics, Kanazawa University) and blunted, and pTERT-E1A-CMV-19K was obtained by ligating the blunted TERT promoter to pΔPr.E1A-CMV-19K. The process thereafter was the same as that in preparing Ad.Surv-E1A-CMV-19K/CMV-EGFP (Ad.Surv-E1A).

Since it is reported that mutated adenovirus in which Rb protein bonding sequence (923-947 bp, 24 bp) in EIA is deleted proliferates in tumor-specific manner (Heise, C et al., Nat. Med. 2000, 6(10): 1134-9), Rb protein binding sequence of the E1A region of the proliferative adenovirus containing survivin may be deleted. E1AΔ24 in which the Rb bonding sequence (for example Ad.Surv-E1AΔ24 in Example 5) is deleted may be obtained by a mutation-introducing method taking advantage of a PCR method (Current Protocols in Molecular Biology, John Wiley & Sons, Inc. 8.5.7 to 8.5.9, 1999) using a primer in which the E1A region is designed from the Rb protein bonding sequence using a plasmid containing at least 5'-side genome of adenovirus as a template. After digesting plasmid pΔPr.E1A-ΔPr.19K with a restriction enzyme, a vector plasmid pΔPr.E1AΔ24-ΔPr.19K in which the Rb protein binding sequence is deleted can be obtained by ligating E1AΔ24 to the digestion product.

The endogenous promoter of the E1B region, for example the promoter of 19 KDa and/or 55 KDa protein coding region, may be substituted with the survivin promoter in the proliferative adenovirus. The proliferative adenovirus containing the survivin promoter is able to induce death of the cell in the infected cells by the virus protein's own toxicity even when the therapeutic gene is not expressed as in Ad.Surv-E1A-CMV-19K. While EGFP in the proliferative adenovirus shown in the examples was introduced in order to facilitate observation of proliferation of the virus in the experiment, higher therapeutic effect may be expected by introducing a therapeutic gene for treating diseases in which survivin is strongly expressed, for example a suicide gene (such as herpes virus thymidine kinase gene) and apoptosis-inducing gene (such as p53 gene).

EXAMPLE 9

Figure 15:
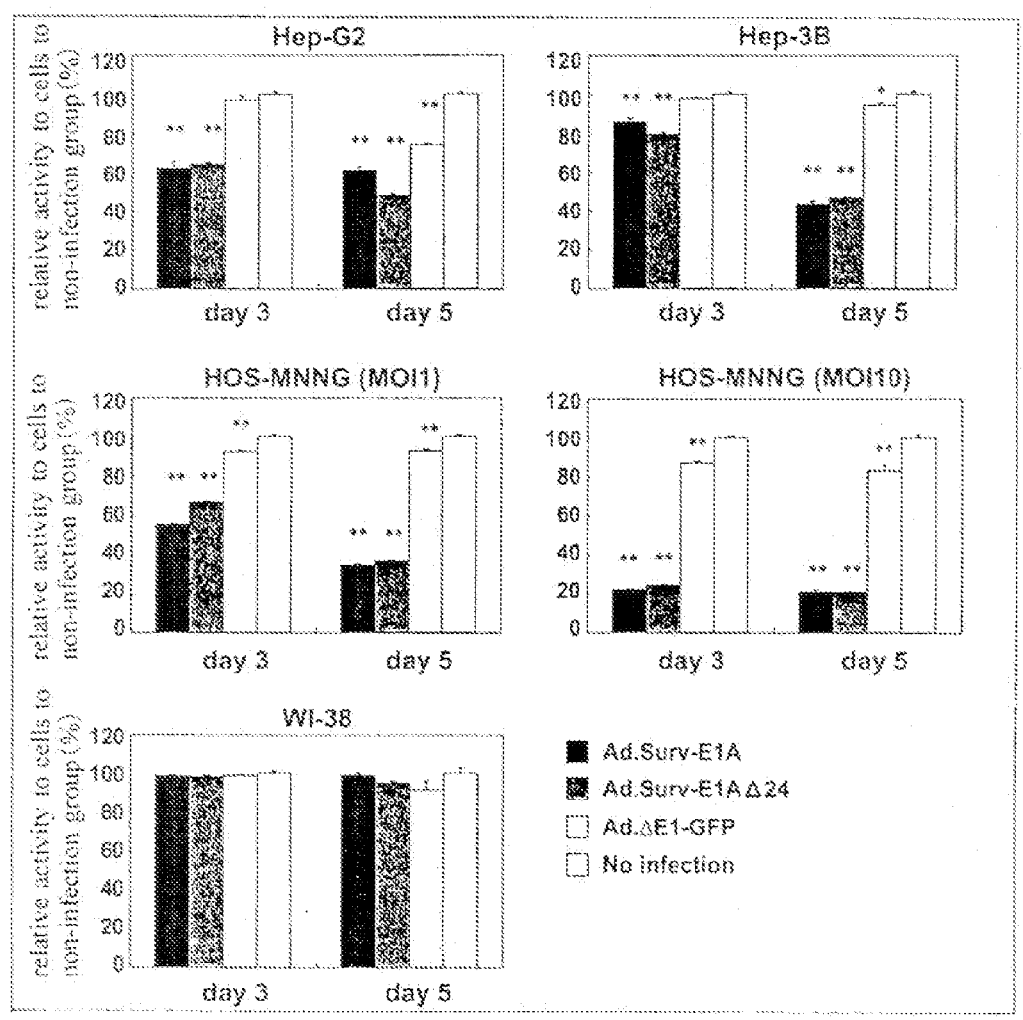
FIG. 15 shows the graphs of analysis of apoptosis induction ratio after infection of various cells with Ad.SurvE1A, Ad.Surv-E1AΔ24 and Ad.ΔE1. The vertical axis shows the survival ratio. *P<0.05 and **P<O.OOI correspond to non-infection groups.

Analysis of Cell Death-Inducing Ability of Proliferative Adenovirus Containing Survivin Promoter in Various Cancer Cells and Normal Cells Various cancer cells (HepG2, Hep3B, HOS-MNNG (MOI 1), HOS-MNNG (MOI 10)) and normal cells 8WI-38) were cultivated on respective 96 well plates, and were infected with Ad.Surv-E1A, Ad.Surv-E1AΔ24 and Ad.ΔE1 at MOI 0.1 (Hep-G2, Hep-3B), MOI 1 (HOS-MNNG, WI-38 and MOI 10 (HOS-MNNG). Cell viability was evaluated 3 and 5 days after the infection using WST-8 (trade name, purchased from Nacalai Tesque Co., catalogue No. 07553-44). The results were shown by relative values taking the value of the non-infected group as 100. As shown in FIG. 15, while both the proliferative vectors Ad.Surv-E1A and Ad.Surv-E1AΔ24 efficiently induced death of the cell in the cancer cells depending on the time and concentration, damage of the normal cells was suppressed to minimum.

The invention is not restricted to the above-mentioned examples so long as other examples are incorporated in the essential scope of the invention.

The invention claimed is:

1. A method for treating a subject having a malignant tumor with high survivin expression, the method comprising directly administering to the malignant tumor an effective amount of a pharmaceutical composition comprising a replication competent adenoviral vector containing an adenoviral genome that includes an E1A gene in which the E1A gene promoter is replaced by the survivin promoter and the survivin promoter is operably linked to the E1A gene.

2. The method of claim 1, wherein the Rb protein binding sequence in the E1A gene is deleted.

3. The method of claim 1, wherein the replication competent adenoviral vector further includes an E1B gene.

4. The method of claim 3, wherein the Rb protein binding sequence in the E1A gene is deleted.

* * * * *

```
                              SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: PCR primer (Synthetic DNA)

<400> SEQUENCE: 1
agatgggcgt ggggcgggac                                                    20

<210> SEQ ID NO 2
<211> LENGTH: 20
<212> TYPE: DNA
<213> ORGANISM: Artificial Sequence
<220> FEATURE:
<223> OTHER INFORMATION: PCR primer (Synthetic DNA)

<400> SEQUENCE: 2
tccgccaaga cgactcaaac                                                    20

<210> SEQ ID NO 3
<211> LENGTH: 56
<212> TYPE: DNA
<213> ORGANISM: Artificial Sequence
<220> FEATURE:
<223> OTHER INFORMATION: PCR primer (Synthetic DNA)

<400> SEQUENCE: 3
tcagtcgcat gcgcggccgc tacgtaacgc gttacccggt gagttcctca agaggc           56

<210> SEQ ID NO 4
<211> LENGTH: 42
<212> TYPE: DNA
<213> ORGANISM: Artificial Sequence
<220> FEATURE:
<223> OTHER INFORMATION: PCR primer (Synthetic DNA)

<400> SEQUENCE: 4
ggacgtccta gggtcgacgc cccatttaac acgccatgca ag                          42

<210> SEQ ID NO 5
<211> LENGTH: 60
<212> TYPE: DNA
<213> ORGANISM: Artificial Sequence
<220> FEATURE:
<223> OTHER INFORMATION: PCR primer (Synthetic DNA)

<400> SEQUENCE: 5
tcagtcccta gggtcgacca tatggatatc caattgcgtg ggctaatctt ggttacatct       60

<210> SEQ ID NO 6
<211> LENGTH: 36
<212> TYPE: DNA
<213> ORGANISM: Artificial Sequence
<220> FEATURE:
<223> OTHER INFORMATION: PCR primer (Synthetic DNA)

<400> SEQUENCE: 6
ggacgtggat ccgcgtctca gttctggata cagttc                                 36
```

<210> SEQ ID NO 7
<211> LENGTH: 36
<212> TYPE: DNA
<213> ORGANISM: Artificial Sequence
<220> FEATURE:
<223> OTHER INFORMATION: PCR primer (Synthetic DNA)

<400> SEQUENCE: 7
tcagtcggat ccgcatgcat ctagagctcg ctgatc                36

<210> SEQ ID NO 8
<211> LENGTH: 70
<212> TYPE: DNA
<213> ORGANISM: Artificial Sequence
<220> FEATURE:
<223> OTHER INFORMATION: PCR primer (Synthetic DNA)

<400> SEQUENCE: 8
ggacgtgaat tcataacttc gtataatgta tgctatatga ggtaattcag aagccataga    60
gcccaccgca                                                           70

<210> SEQ ID NO 9
<211> LENGTH: 32
<212> TYPE: DNA
<213> ORGANISM: Artificial Sequence
<220> FEATURE:
<223> OTHER INFORMATION: PCR primer (Synthetic DNA)

<400> SEQUENCE: 9
tcagtcgtcg accgttgaca ttgattattg ac                    32

<210> SEQ ID NO 10
<211> LENGTH: 32
<212> TYPE: DNA
<213> ORGANISM: Artificial Sequence
<220> FEATURE:
<223> OTHER INFORMATION: PCR primer (Synthetic DNA)

<400> SEQUENCE: 10
ggacgtcaat tggcttgggt ctccctatag tg                    32

<210> SEQ ID NO 11
<211> LENGTH: 20
<212> TYPE: DNA
<213> ORGANISM: Artificial Sequence
<220> FEATURE:
<223> OTHER INFORMATION: PCR primer (Synthetic DNA)

<400> SEQUENCE: 11
gcatgggtgc cccgacgttg                                  20

<210> SEQ ID NO 12
<211> LENGTH: 20
<212> TYPE: DNA
<213> ORGANISM: Artificial Sequence
<220> FEATURE:
<223> OTHER INFORMATION: PCR primer (Synthetic DNA)

<400> SEQUENCE: 12
gctccggcca gaggcctcaa                                  20

<210> SEQ ID NO 13
<211> LENGTH: 23
<212> TYPE: DNA
<213> ORGANISM: Artificial Sequence

```
<220> FEATURE:
<223> OTHER INFORMATION: PCR primer (Synthetic DNA)

<400> SEQUENCE: 13
ttcctgcact ggctgatgag tgt                                            23

<210> SEQ ID NO 14
<211> LENGTH: 21
<212> TYPE: DNA
<213> ORGANISM: Artificial Sequence
<220> FEATURE:
<223> OTHER INFORMATION: PCR primer (Synthetic DNA)

<400> SEQUENCE: 14
cgctcggccc tcttttctct g                                              21
```